(12) United States Patent
Davis

(10) Patent No.: US 6,483,590 B1
(45) Date of Patent: Nov. 19, 2002

(54) INSTRUMENT FOR RAPIDLY CHARACTERIZING MATERIAL REFLECTANCE PROPERTIES

(75) Inventor: Keith J. Davis, Seattle, WA (US)

(73) Assignee: The Boeing Company, Chicago, IL (US)

( * ) Notice: Subject to any disclaimer, the term of this patent is extended or adjusted under 35 U.S.C. 154(b) by 170 days.

(21) Appl. No.: 09/740,316

(22) Filed: Dec. 18, 2000

(51) Int. Cl.[7] .............................................. G01N 21/55
(52) U.S. Cl. ........................ 356/445; 356/446; 356/600
(58) Field of Search ................................ 356/445, 446, 356/600; 250/339.11, 341.8

(56) References Cited

U.S. PATENT DOCUMENTS

| | | | |
|---|---|---|---|
| 4,277,177 A | | 7/1981 | Larsen et al. ............... 356/431 |
| 4,360,275 A | * | 11/1982 | Loudeback ................. 356/446 |
| 4,518,259 A | * | 5/1985 | Ward .......................... 356/446 |
| 4,660,984 A | * | 4/1987 | MacDonald ................ 356/446 |
| 4,661,706 A | | 4/1987 | Messerschmidt et al. ... 250/341 |
| 4,815,858 A | | 3/1989 | Snail .......................... 356/446 |
| 4,988,205 A | | 1/1991 | Snail .......................... 356/446 |
| 5,505,543 A | | 4/1996 | Webbeking et al. ........... 374/9 |
| 5,517,315 A | * | 5/1996 | Snail et al. ................. 356/445 |
| 5,605,838 A | | 2/1997 | Backhaus et al. ............. 436/34 |
| 5,637,873 A | | 6/1997 | Davis et al. ........... 250/339.11 |
| 5,659,397 A | | 8/1997 | Miller et al. ................ 356/446 |

* cited by examiner

Primary Examiner—Georgia Epps
Assistant Examiner—M. Hasan
(74) Attorney, Agent, or Firm—Harness, Dickey & Pierce, P.L.C.

(57) ABSTRACT

A reflectometer characterizes the reflectance properties of a test material. The reflectometer includes a radiation subsystem that generates and directs radiation onto a test material at a plurality of incident angles. An elliptical reflector assembly has one or more reflectors with a first and second foci. A holder positions the test material at the first focus of the reflectors. One or more lenses are located within a first focal length of the second focus of the reflectors. The lenses receive a first angular image that is reflected by the reflector. The holder is rotatable relative to the radiation subsystem. Stepper motors and encoders vary the angular position of the incident angle and an azimuth angle of the test material. A computer records an angular image for each azimuth and incident angle to completely characterize the reflectance properties of the test material.

24 Claims, 16 Drawing Sheets

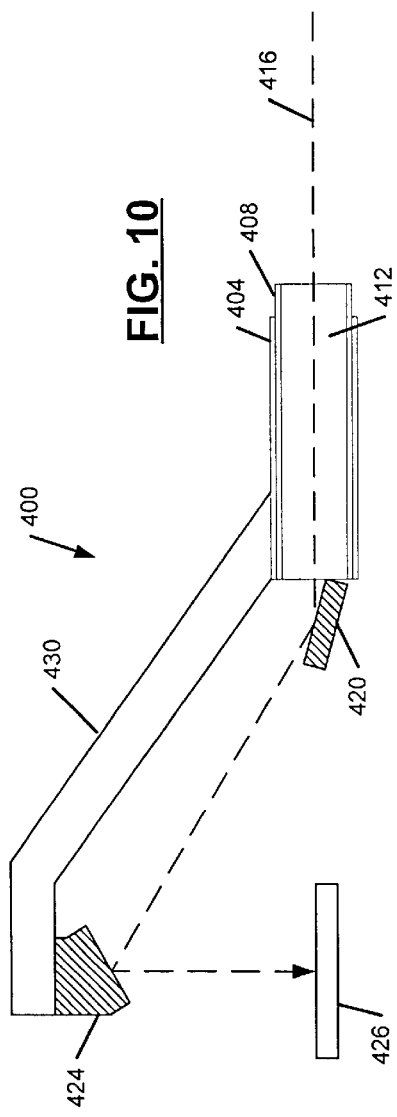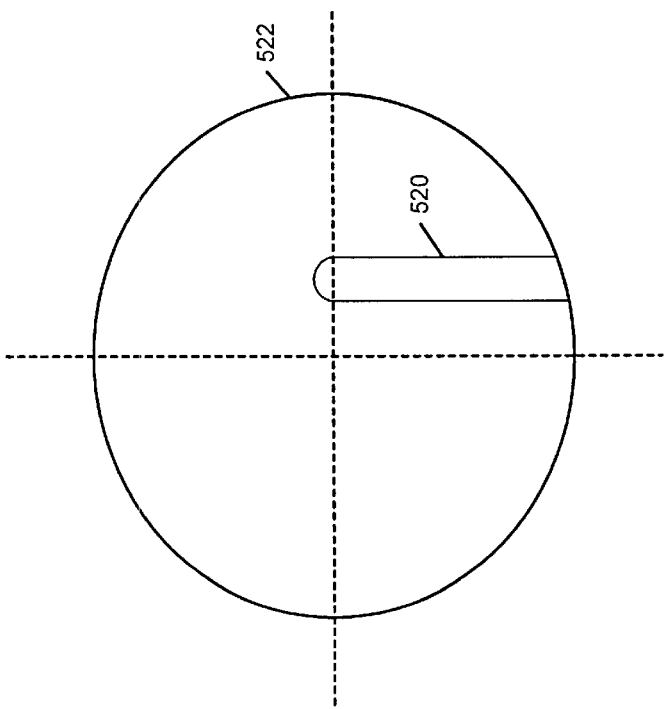

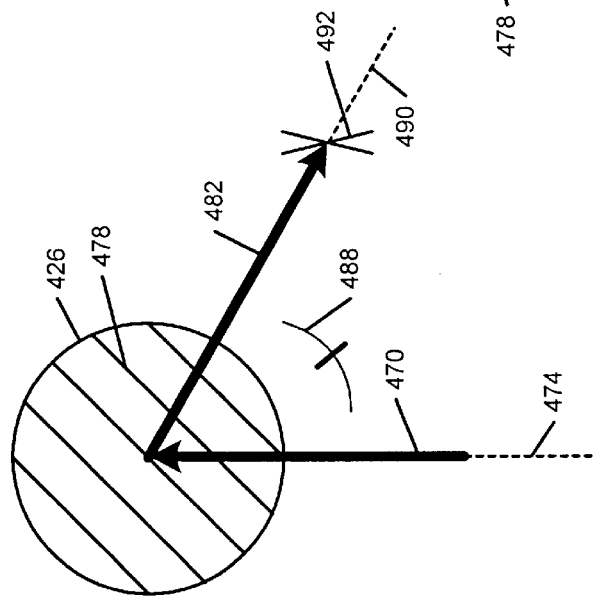
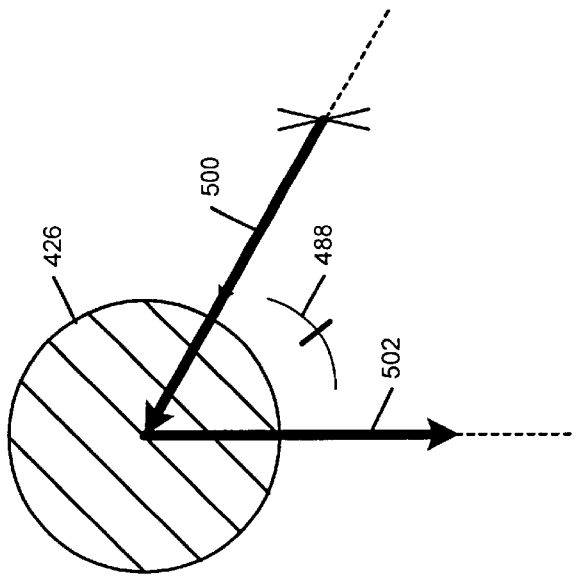
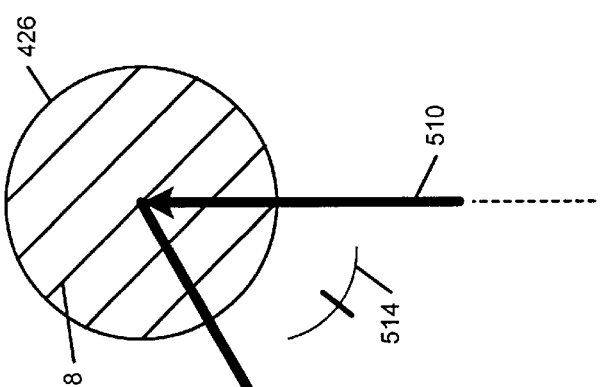
FIG. 15A
FIG. 15B
FIG. 15C

US 6,483,590 B1

INSTRUMENT FOR RAPIDLY CHARACTERIZING MATERIAL REFLECTANCE PROPERTIES

TECHNICAL FIELD

The present invention relates to reflectometers for measuring the reflectance of a test material. More particularly, the present invention relates to reflectometers that measure the angular distribution pattern of light reflecting off the test material.

BACKGROUND OF THE INVENTION

In a number of disciplines such as remote sensing, computer graphics, and aircraft signature prediction, the reflection properties of materials must be precisely determined. In particular, the bidirectional reflectance distribution function (BRDF) defines the distribution of the reflected light rays that are associated with each possible incident direction of light. For a particular wavelength of light, the BRDF is a function of four variables. Two of the variables define the direction of incident light. The remaining two variables define the direction of reflected light. For isotropic materials, the BRDF is independent of the azimuth orientation of the sample. Therefore, for isotropic materials, only three angles are needed to describe the BRDF. Anisotropic materials, however, require the four variables to describe the BRDF and are much more difficult to characterize.

In practice, the BRDF of anisotropic materials is extremely difficult to measure with any degree of completeness due to the large number of angle combinations for the incident and reflected light. For example, if the BRDF measurements were made by moving a light source and a detector in two degree increments, over 65 million separate measurements are required. If each individual measurement could be accomplished in one second, the complete BRDF measurements would take over 2 years.

Surface Optics markets a portable measurement device that operates in the infrared (IR) region. The portable measurement device uses a movable source and detector. Furthermore, in U.S. Pat. No. 5,637,873, which is incorporated by reference, a hand-held instrument uses angular imaging to measure the directional reflectance of materials after they have been applied to a vehicle. This instrument is suitable for verifying compliance of in situ coatings with their reflectance specifications. Both devices, however, do not provide a complete and automated characterization of the BRDF of a material.

SUMMARY OF THE INVENTION

A reflectometer according to the invention characterizes the reflectance properties of a test material. The reflectometer includes a radiation subsystem that generates and directs radiation onto a test material at a plurality of incident angles. An elliptical reflector assembly has one or more reflectors with first and second foci. A holder positions the test material at the first foci of the reflectors. One or more lenses are located within a first focal length of the second focus of the reflectors. The lenses receive angular images that are reflected by the reflectors.

According to other features of the invention, the elliptical reflector assembly includes a first reflector having first and second foci and a second reflector having a third and fourth foci. A first lens is located at said second focus of said first reflector. A second lens is located at said fourth focus of said second reflector. The holder positions the test material at the first and third foci of the first and second reflectors.

According to other features of the invention, the holder is rotatable relative to the radiation subsystem. The radiation subsystem includes a housing that is movable relative to the elliptical reflector assembly to alter the incident angle. A focusing mirror is connected to the housing. A slit controls the shape of the radiation that is illuminated by the test material. The slit is movable relative to the housing to keep the shape and size of the illumination spot relatively constant as the housing moves.

According to still other features of the invention, a shutter blocks the radiation when in a closed position and passes the radiation when the shutter is in an open position. Ambient reflection and sample emissions measurements are made when the shutter is in the closed position.

According to still other features of the invention, a first stepper motor adjusts an angular position of the housing relative to the elliptical reflector assembly to adjust an incident angle of the radiation on the test material. A position encoder generates a position signal that is related to the angular position of the housing.

According to still other features of the invention, a second stepper motor adjusts an angular position of the holder. A second position encoder generates a position signal that is related to the angular position of the holder.

In still other features of the invention, a computer is connected to the first and second stepper motors. The computer is also connected to the first and second position encoders. A first imaging assembly receives the first angular image and generates a first angular image signal. A second imaging assembly receives the second angular image and generates a second angular image signal. The computer generates a first difference signal by subtracting an ambient first image signal from the first image signal. The computer generates a second difference signal by subtracting an ambient second image signal from the second image signal. The computer generates a calibrated first product signal by multiplying the first difference signal by a first set of calibration factors. The computer generates a calibrated second product signal by multiplying the second difference signal by a second set of calibration factors. The computer combines the calibrated first difference signal with the calibrated second difference signal to create a hemispherical angular image signal.

Other objects, features and advantages will be apparent from the specification, the drawings and claims.

BRIEF DESCRIPTION OF THE DRAWINGS

The various advantages of the present invention will become apparent to one skilled in the art by reading the following specification and subjoined claims and by referencing the following drawings in which:

FIG. 10 is a side cross-sectional view of a mirror arm according to an alternate embodiment of the present invention;

FIGS. 15A–15C illustrate the reciprocity principle by showing incident and reflected light on an anisotropic material;

FIG. 16 illustrates a plan view of a ellipsoid mirror with an offset slot; and

DETAILED DESCRIPTION OF THE PREFERRED EMBODIMENTS

The ensuing detailed description provides preferred exemplary embodiments only and is not intended to limit the scope, applicability, or configuration of the invention. Rather, the ensuing detailed description of the preferred exemplary embodiments will provide those skilled in the art with an enabling description for implementing a preferred exemplary embodiment of the invention. It being understood that various changes may be made in the function and arrangement of elements without departing from the spirit and scope of the invention as set forth in the appended claims.

Figure 1:
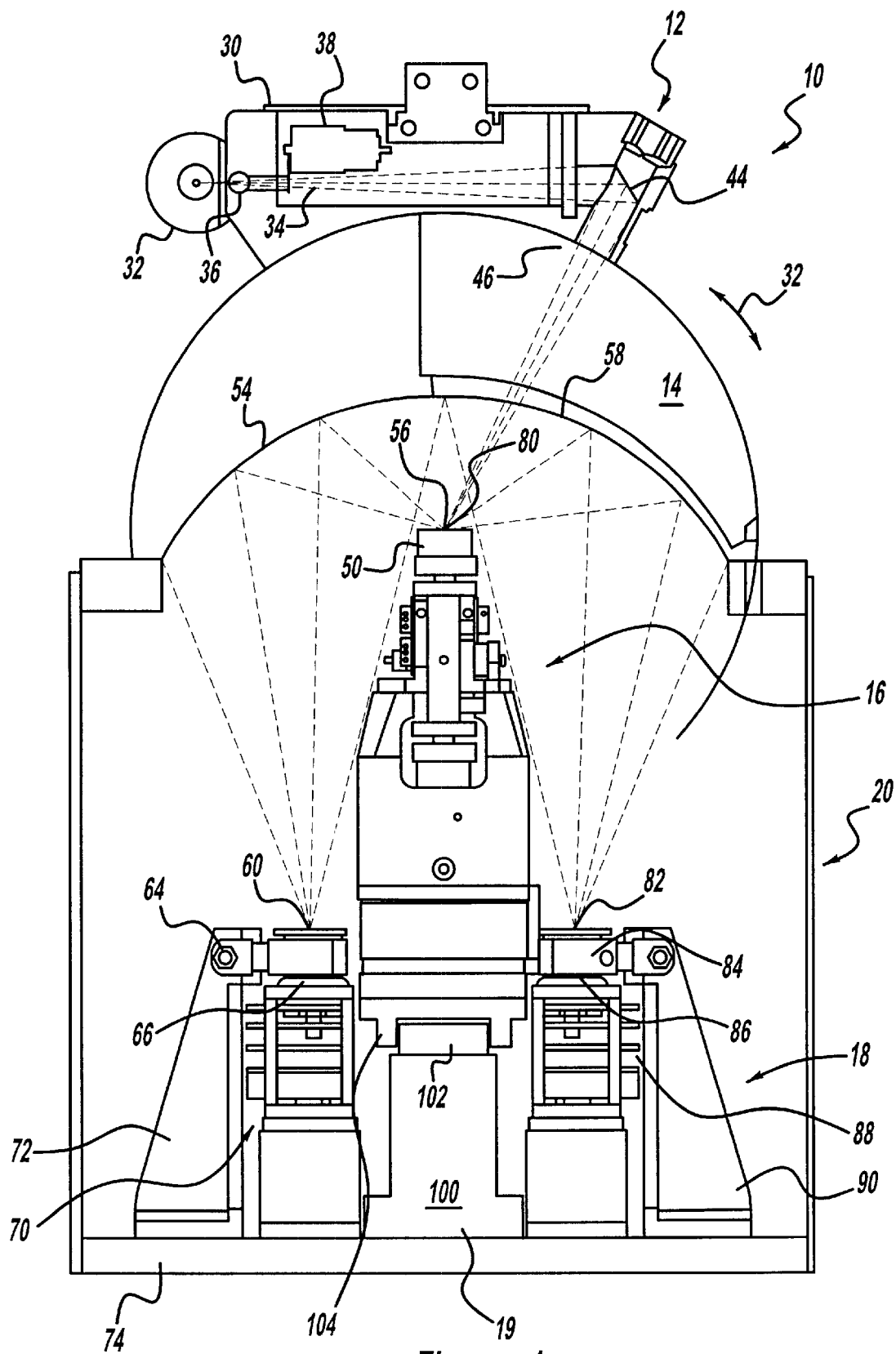
FIG. 1 is a cross-sectional view of an imaging reflectometer according to the present invention.

Referring now to FIG. 1, an imaging reflectometer 10 is illustrated and includes a radiation source assembly 12, an elliptical reflector assembly 14, a test material positioning assembly 16, a lens positioning assembly 18, a translation stage 19, and an enclosure 20.

The radiation source assembly 12 includes a radiation source housing 30 that is movable in directions indicated by arrow 31. The radiation source assembly 12 further includes a radiation source 32 that provides radiation that illuminates a slit 36 to produce a beam. A shutter 38 selectively blocks and passes the beam 34. Baseline or ambient radiation measurements are made with the shutter 38 blocking the beam 34. The baseline measurements are subtracted from subsequent measurements to remove system background radiation. An elliptical reflector 44 reflects and focuses the beam 34 through a slot 46 in the elliptical reflector assembly 14 onto a test material 50. In a preferred mode, the radiation source assembly 12 rotatably moves to provide an angle of incidence of the beam 34 relative to the test material 50 that is between 90° and 0°.

The elliptical reflector assembly 14 includes a forward or first elliptical reflector 54 having a first focus 56 that is located at a target area on the test material 50. A second focus 60 is located above a lens and filter assembly 64. Preferably the second focus 60 is located approximately within one focal length of the lens and filter assembly 64. The lens collimates radiation that is received from the first elliptical reflector 54. An imaging array 66 receives the first angular image from the lens assembly 64. Image processing electronics 70 are connected to the imaging array 66. The lens and filter assembly 64 is adjustably connected to a base bracket 72 that is connected to a bottom surface 74 of the imaging reflectometer 10.

The backward or second elliptical reflector 58 has a third focus 80 that is located at the target area on the test material 50 and a fourth focus 82 that is located above a lens and filter assembly 84. Preferably, the fourth focus 82 is located approximately within one focal length of the lens and filter assembly 84. The lens collimates radiation that is received from the second elliptical reflector 58. An imaging array 86 receives the second angular image from the lens and filter assembly 64. Image processing electronics 88 are connected to the imaging array 86. A lens and filter assembly 84 is adjustably connected to a base bracket 90 that is connected to the bottom surface 74 of the imaging reflectometer 10.

The translation stage 19 includes a translation base 100 that is connected to the bottom surface 74. A male translation guide 102 is slideably connected to a female translation guide 104. The female translation guide 104 is connected to the test material positioning assembly 16. The translation base 100, the male translation guide 102, and the female translation guide 104 allow the test material positioning assembly 16 to be moved between a measurement position and an adjustment position that are shown and described in FIG. 3.

Figure 2:
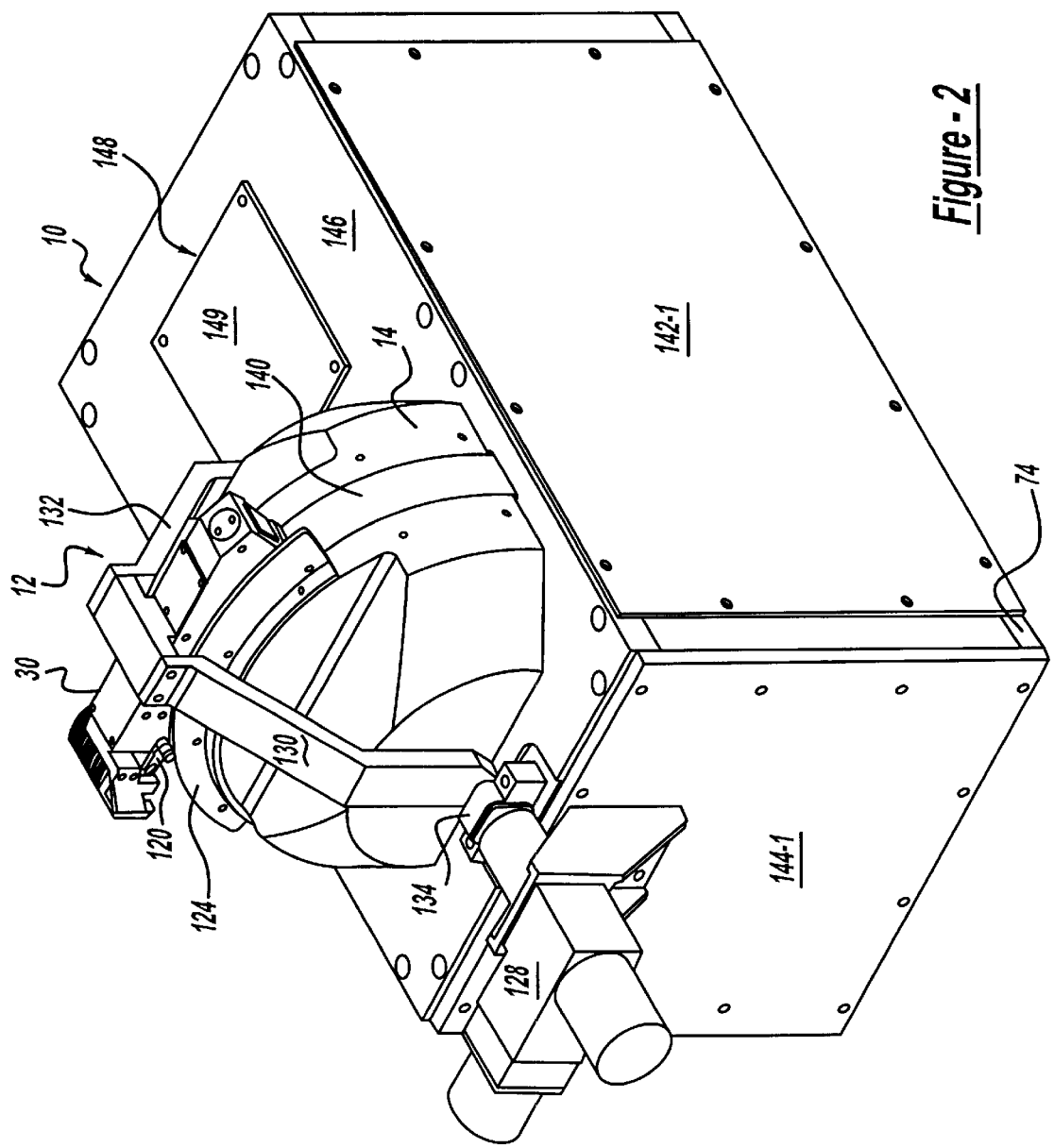
FIG. 2 is a perspective view of an exterior of the imaging reflectometer of FIG. 1.

Referring now to FIG. 2, the imaging reflectometer 10 is illustrated in further detail. An arm 120 is biased by an adjustment cam 124 to vary the angular position of the slit 36 relative to the beam 34 to control the size of the beam spot on the test material 50. In a preferred mode, the beam spot is approximately 2 millimeters (mm) by 2 mm. As the angle of incidence varies between 90° to 0°, the angular position of the slit 36 adjusts to maintain a constant-sized beam spot on the target area of the test material 50.

A stepper motor 128 controllably rotates arms 130 and 132 relative to an axis that is defined by bearings 134. The stepper motor 128 preferably includes a position encoder for generating a position signal that is related to the relative angular position of the arms 130 and 132. A slot cover 140 covers the slot 46 and is movable with the radiation source housing 30.

The enclosure 20 includes sides 142-1 and 142-2 and ends 144-1 and 144-2. A top 146 includes an access opening 148 and cover 149 for accessing the interior of the enclosure 20, for example when the test material positioning assembly 16 is in the adjustment position. The stepper motor 128 is attached to the enclosure 20 adjacent to the end 144-1 and the top 146.

Figure 3:
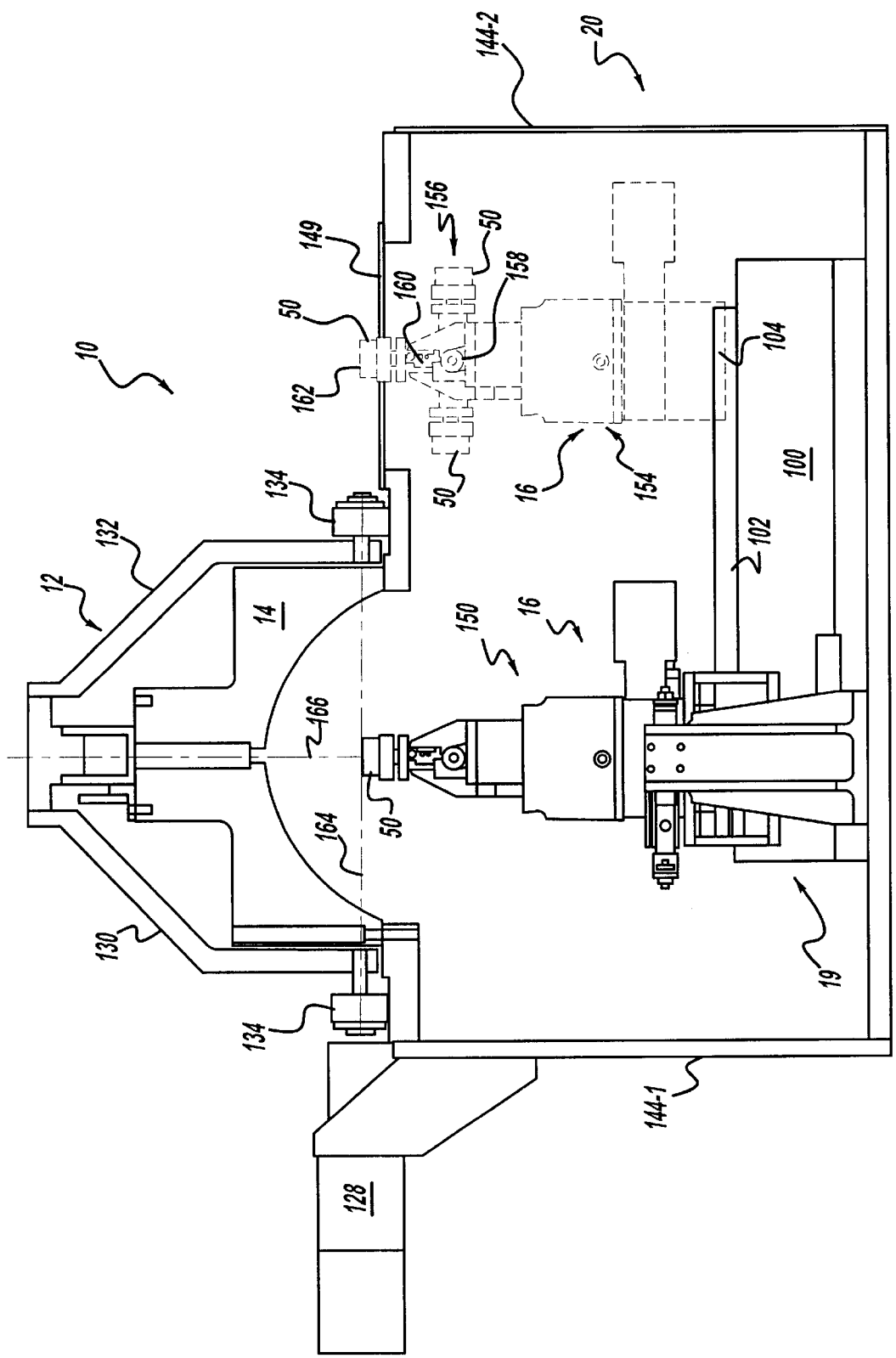
FIG. 3 is a side view of the imaging reflectometer of FIG. 1 that shows a measurement position and an adjustment position.

Referring now to FIG. 3, the test material positioning assembly 16 of the imaging reflectometer 10 can be positioned in the measurement position 150 and the adjustment position 154. An upper portion 156 of the test material positioning assembly 16 is rotatable about an axis 158. The upper portion 156 is rotatable 90° in first and second directions to provide additional clearance when moving between the measurement and adjustment positions 150 and 154, respectively. A height adjustment device 160 of the test material positioning assembly 16 allows an upper surface 162 of the test material 50 to be positioned at the height of a target plane 164. The translation stage 19 also allows the test material to be positioned relative to a center line 166. The upper portion 156 is an arm with two equivalent ends, each of which can hold a test sample. One of these ends can be used to hold a reference material of known reflectance to verify the stability of the calibration.

Figure 4:
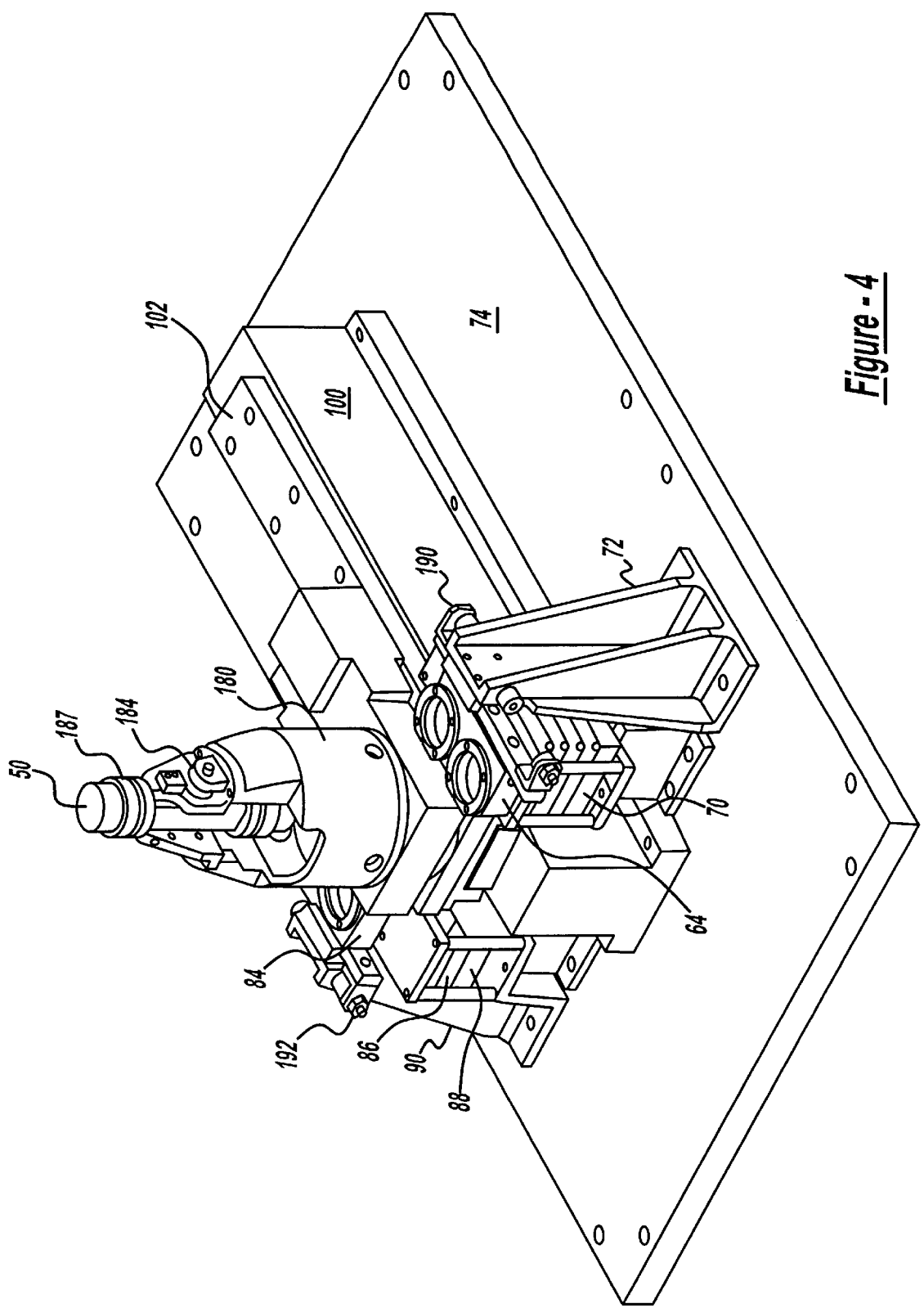
FIG. 4 is a perspective view of a test material positioning assembly, lenses, imaging arrays, and image processing electronics.

Referring now to FIG. 4, a positioner housing 180 sits on top of a rotation stage 184 to rotate a test material holder 187 on which the test material 50 sits. A position encoder connected to the rotation motor generates a rotation signal that is related to an azimuth angle of the test material 50. Translation assemblies 190 and 192 permit the manual interchanging of two lens/filter combinations corresponding to two different wavelength bands.

Figure 5:
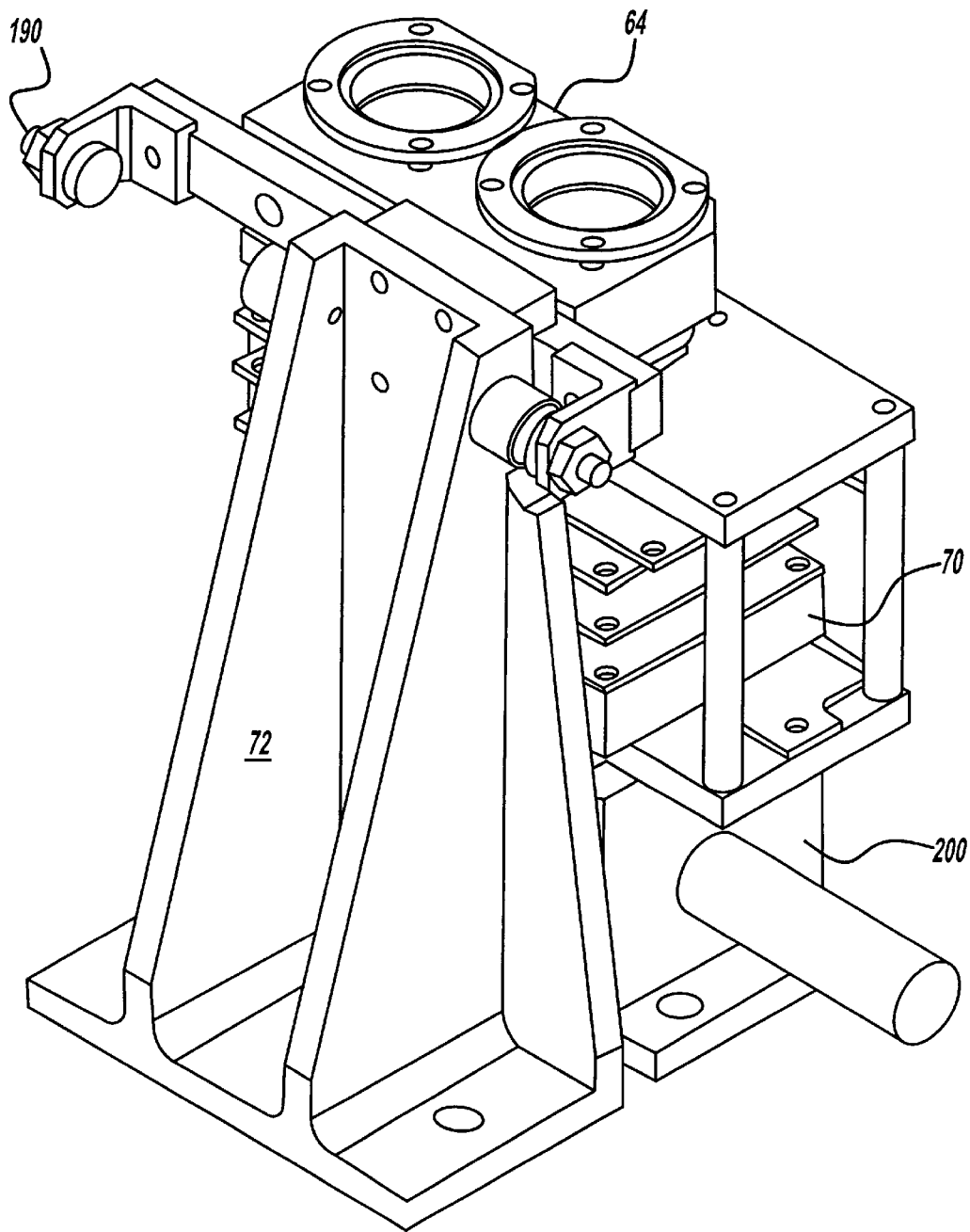
FIG. 5 is a perspective view of an imaging array and lens assembly.
Figure 6B:
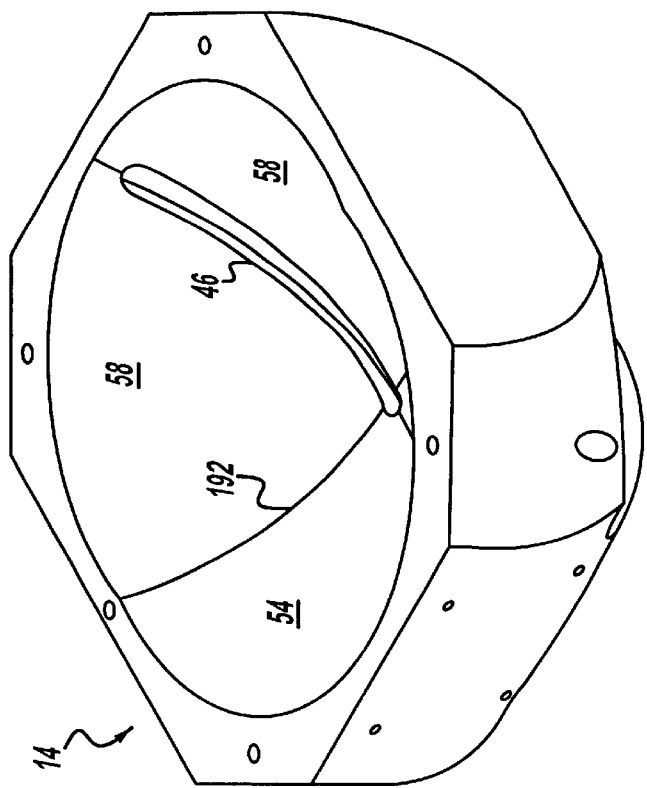
FIG. 6B is a bottom-side, perspective view of the elliptical reflector assembly.
Figure 6A:
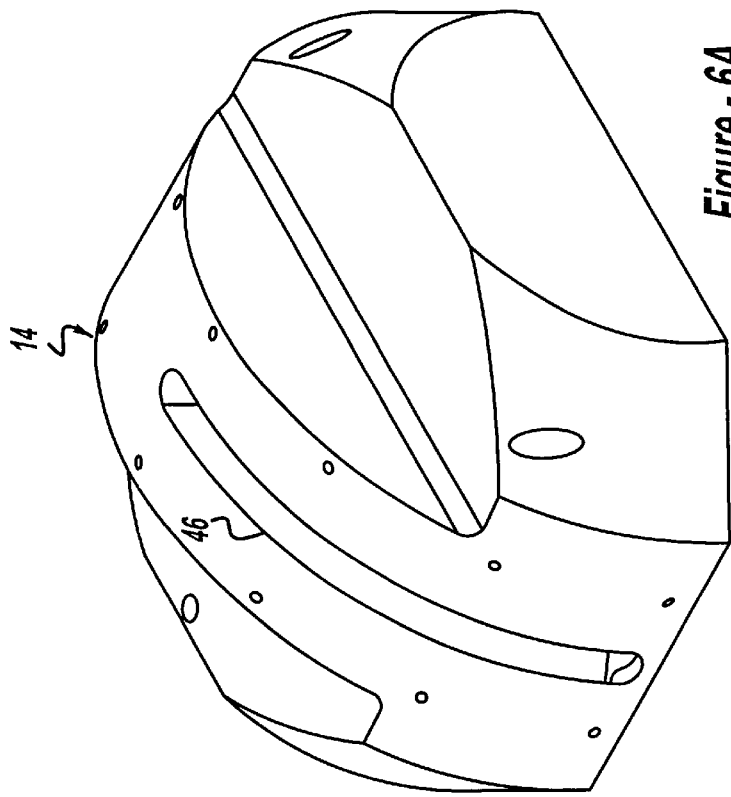
FIG. 6A is a top-side, perspective view of an elliptical reflector assembly.

Referring now to FIG. 5, a vertical translation stage 200 allows the adjustment of the lens and filter assembly 64 in a vertical direction. The translation assembly 190 allows the adjustment of the lens and filter assembly 64 in a horizontal direction as well as interchange of the two lens/filter combinations. Referring now to FIG. 6, the elliptical reflector assembly 14 is illustrated in further detail. A cusp 192 separates the first elliptical reflector 54 from the second elliptical reflector 58. The slot 46 allows the beam 34 to pass through the elliptical reflector assembly 14 onto the test material 50.

Figure 7:
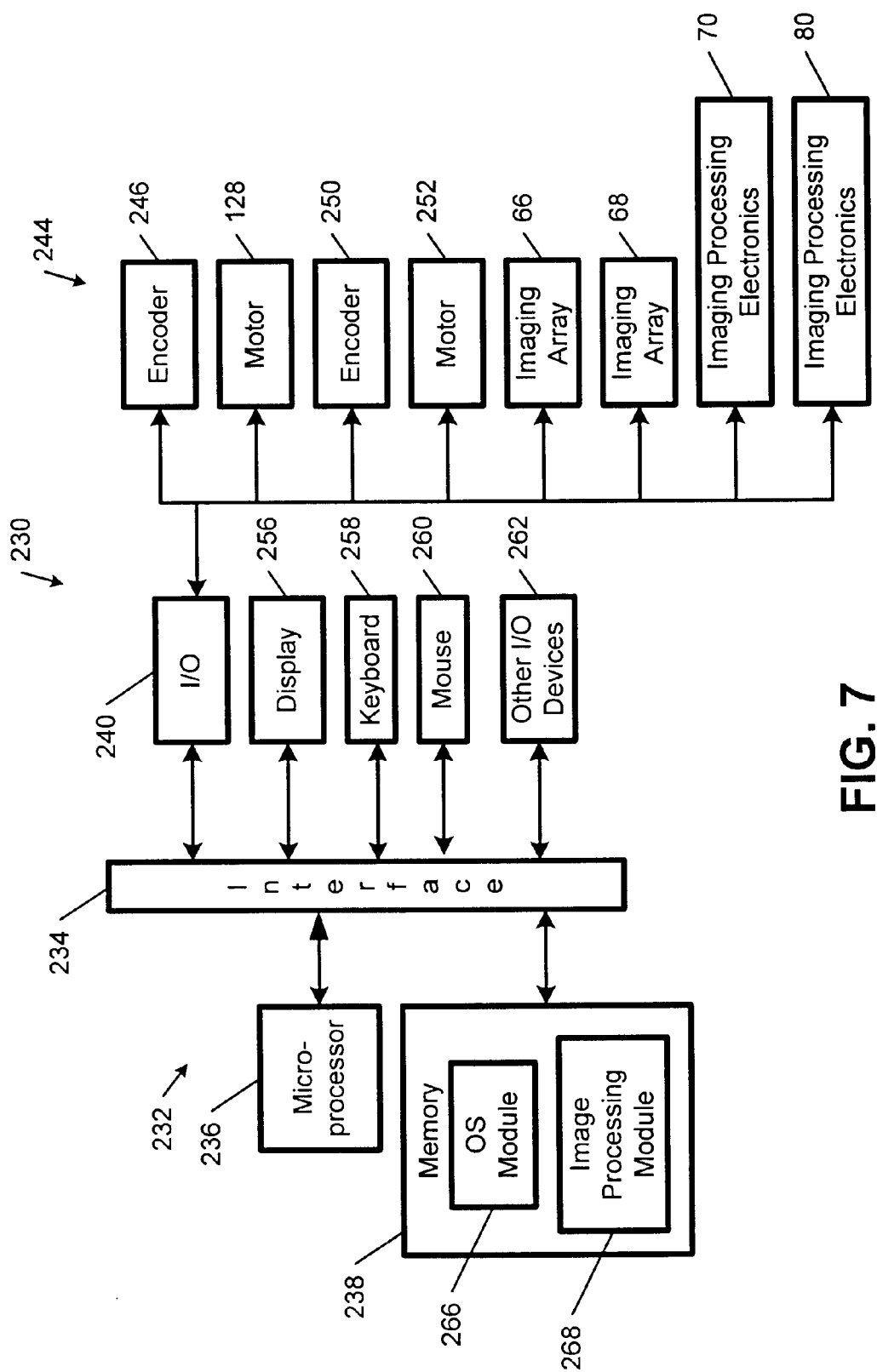
FIG. 7 is a schematic diagram of a computer for controlling the automated BRDF characterization of a test material.

Referring now to FIG. 7, a control system for automating the BRDF characterization for the test material 50 is illustrated at 230. The control system 230 includes a controller with an input/output (I/O) interface 234, a microprocessor 236 and memory 238. The memory 238 includes random access memory (RAM), read only memory (ROM), and/or external storage such as a hard drive, a floppy drive, optical storage or other suitable electronic memory storage. An additional I/O card 240 may be provided for connecting peripheral devices 244. Alternatively, the peripheral devices 244 can be directly connected to the I/O interface 234.

The peripheral devices 244 include a position encoder 246 and the stepper motor 128 that are associated with the radiation source assembly 12. The position encoder 246 is associated with the stepper motor 128. As the stepper motor 128 incrementally changes the angle of incidence of the beam 34 on the target area of the test material 50, the position encoder 246 generates an angular position signal.

The peripheral devices 244 further include an encoder 250 that is associated with the rotation stage 184 and a stepper motor 252. As the stepper motor 252 rotates the test material holder 187 and the test material 50, the position encoder 250 generates an azimuth angle signal. The control system 230 controllably adjusts the stepper motors 128 and 252 when measuring the BRDF as will be described further.

The peripheral devices 244 further include the imaging arrays 66 and 86 and/or the image processing electronics 70 and 80 that are likewise connected to the I/O card 240 and/or the I/O interface 234. A display 256, a keyboard 258 and a mouse 260 are also connected to the I/O interface 234. Other I/O devices 262 such as printers, scanners, and other suitable devices are connected to the I/O interface 234. The memory 238 loads an operating system (OS) module 266 when booted up. An image processing module 268 is also loaded into the memory 238 during use. In a preferred embodiment, the control system 230 is a computer.

Figure 8:
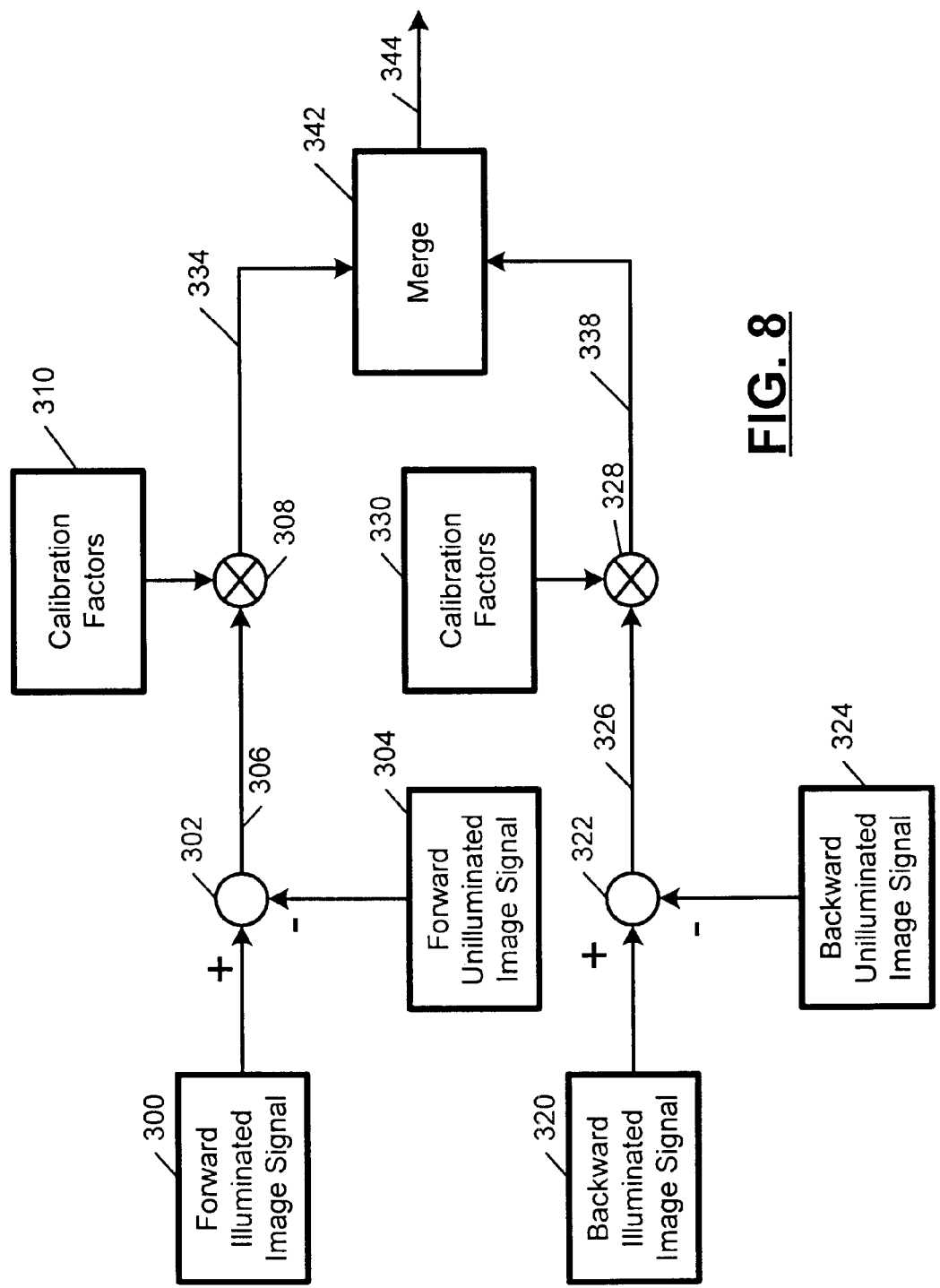
FIG. 8 is a data flow diagram illustrating the processing of the BRDF characterization.

Referring now to FIG. 8, the first imaging array 66 and image processing electronics 70 generate a first illuminated image signal 300 when the shutter 38 is open and the radiation source 32 is on. The first illuminated image signal 300 is input to a difference calculator 302. A first unilluminated or ambient image signal that is output by the first image processing electronics 70 when the shutter 38 is closed is subtracted using the difference calculator 302. The first difference signal 306 is input to a first input of a product calculator 308. Calibration factors 310 are input to a second input of the product calculator 308.

The calibration factors are set by using a sample diffuse gold reflector with a known reflectance. The intensity value corresponding to each pixel of the image are measured and a calibration factor is computed to provide the known or expected BRDF. These same calibration factors are then used for computing the BRDF for the test material 50.

A second illuminated image signal 320 is output by the second image processing electronics 80 when the shutter 38 is open. The second illuminated image signal 320 is input to a second difference calculator 322. A second unilluminated or ambient image signal 324 that is output when the shutter 38 is closed is input to the difference calculator 322. A second difference signal 326 is input to a first input of a second product calculator 328. Calibration factors 330 are likewise input to the second product calculator 328.

A first calibrated product signal 334 is output by the product calculator 308. A second calibrated product signal 338 is also output by the second product calculator 328. A merge calculator 342 merges the first and second calibrated product signals 334 and 338. A hemispherical image signal 344 is output by the merge calculator 342. The hemispherical image signal 344 is an angular image of all of the radiation that is reflected into an upper hemisphere above the test material except for light that hits the slot 46 in the elliptical reflector assembly 14. With the exception retro-reflection in the slot area, the BRDF that is generated completely characterizes the reflectance properties of the sample.

Figure 9:
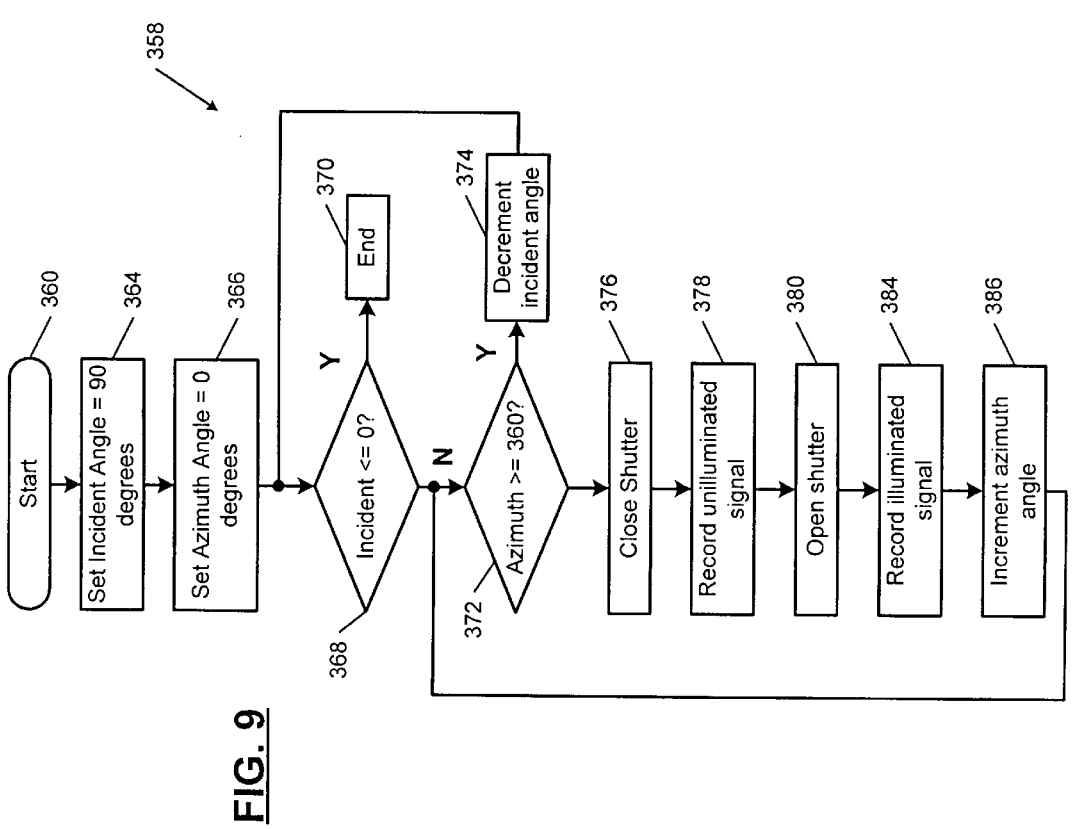
FIG. 9 is a flowchart illustrating steps for characterizing the BRDF of a test material.

Referring now to FIG. 9, the steps for automatically controlling the first and second stepper motors 128 and 252 when characterizing the BRDF of the test material 50 is shown and is generally designated 358. Control starts at step 360. In step 364, the incident angle is set equal to 90 degrees. In step 366, the azimuth angle is set equal to zero degrees. In step 368, control determines whether the incident angle is less than or equal to zero degrees. If it is, control ends at step 370. Otherwise, control continues with step 372 where control determines if the azimuth angle is greater than or equal to 360 degrees. If it is, control decrements the incident angle in step 374. Otherwise, the shutter is closed in step 376. In step 378, an unilluminated signal is recorded. In step 380, the shutter is open. In step 384, the illuminated signal is recorded. In step 386, the azimuth angle is incremented. Control continues from step 386 to step 372.

Referring now to FIG. 10, an alternate mirror arm 400 is shown and includes a hub 404 that is rotatably mounted on a bearing 408. The alternate mirror arm 400 does not require a slot in the elliptical reflector assembly. The hub 404 and the bearing 408 define an open central cavity 412 through which an incident beam of light 416 travels. A first mirror 420 and a second mirror 424 redirect the light 416 onto a sample 426. The sample 426 can be isotropic or anisotropic. The first and second mirrors 420 and 424 are connected to and supported by an arm portion 430 that extends from the hub 404.

Figure 11:
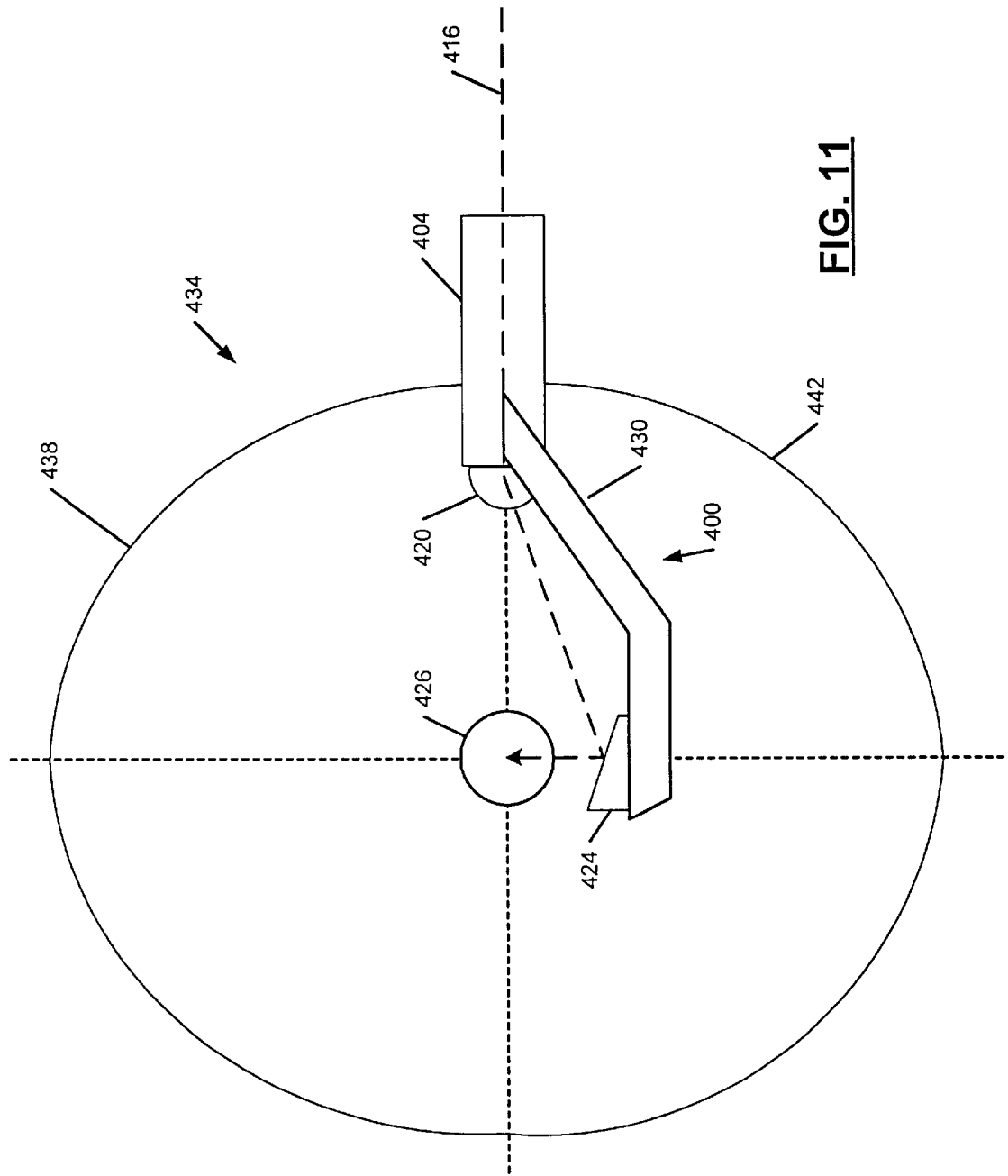
FIG. 11 is a plan view illustrating the mirror arm of FIG. 10 used with a double ellipsoid mirror.
Figure 12:
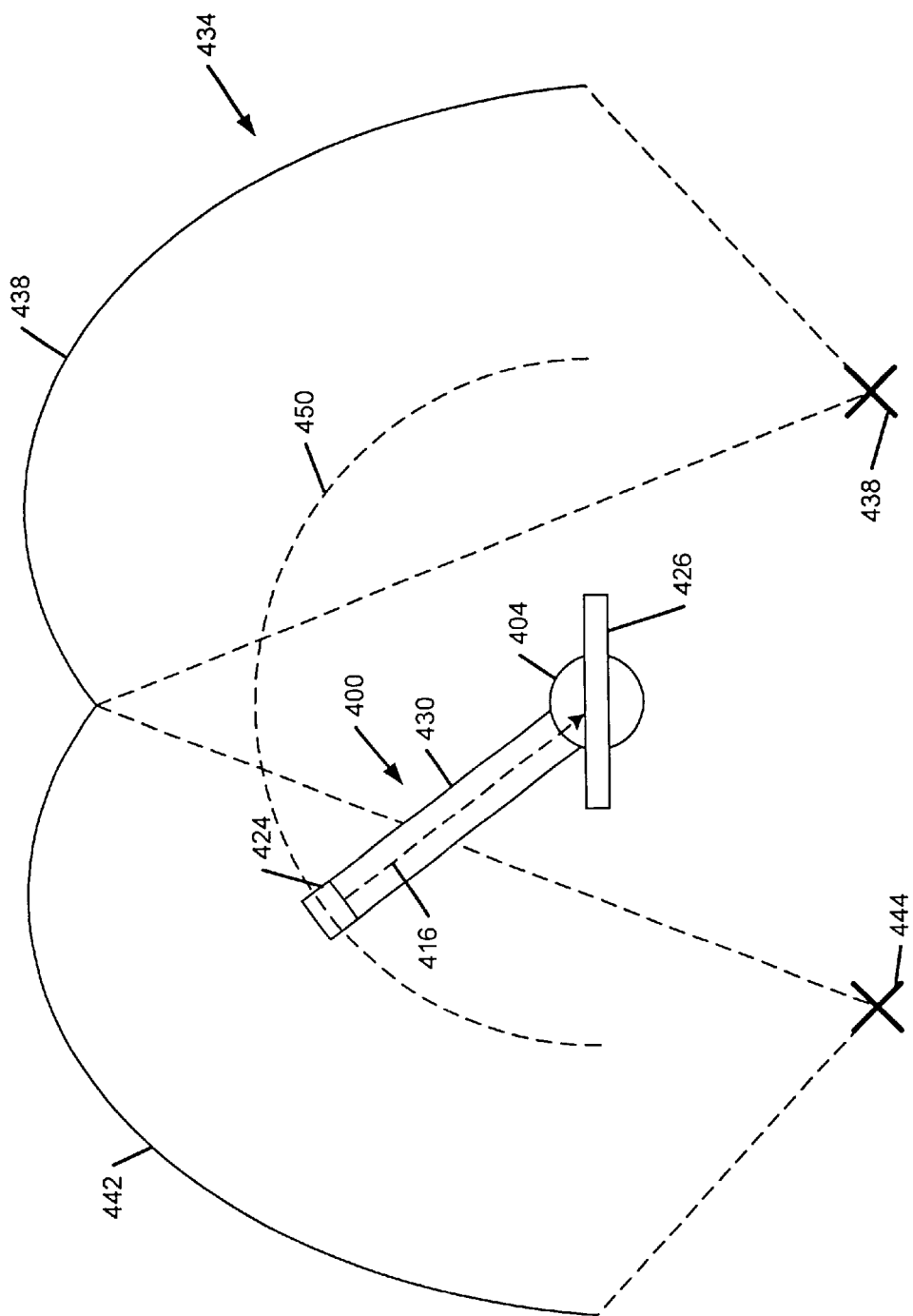
FIG. 12 is a side view of the mirror arm and the double ellipsoid mirror of FIG. 11.

Referring now to FIGS. 11 and 12, the mirror arm 400 is shown rotatably mounted inside of a double ellipsoid mirror 434 (which is similar to the elliptical reflector assembly shown above without a slot). The double ellipsoid mirror 434 includes a front half hemisphere 438 having a first focus 440 and a rear half hemisphere 442 having a second focus 444. The mirror arm 400 sweeps through an arc 450 as it rotates on the bearings 408. A driving mechanism such as a belt and pulley, a geared mechanism or any other suitable driving mechanism can be used to position the mirror arm 400. A position encoder can also be employed to generate a rotational position signal that is used as an input signal for a controller.

Figure 13:
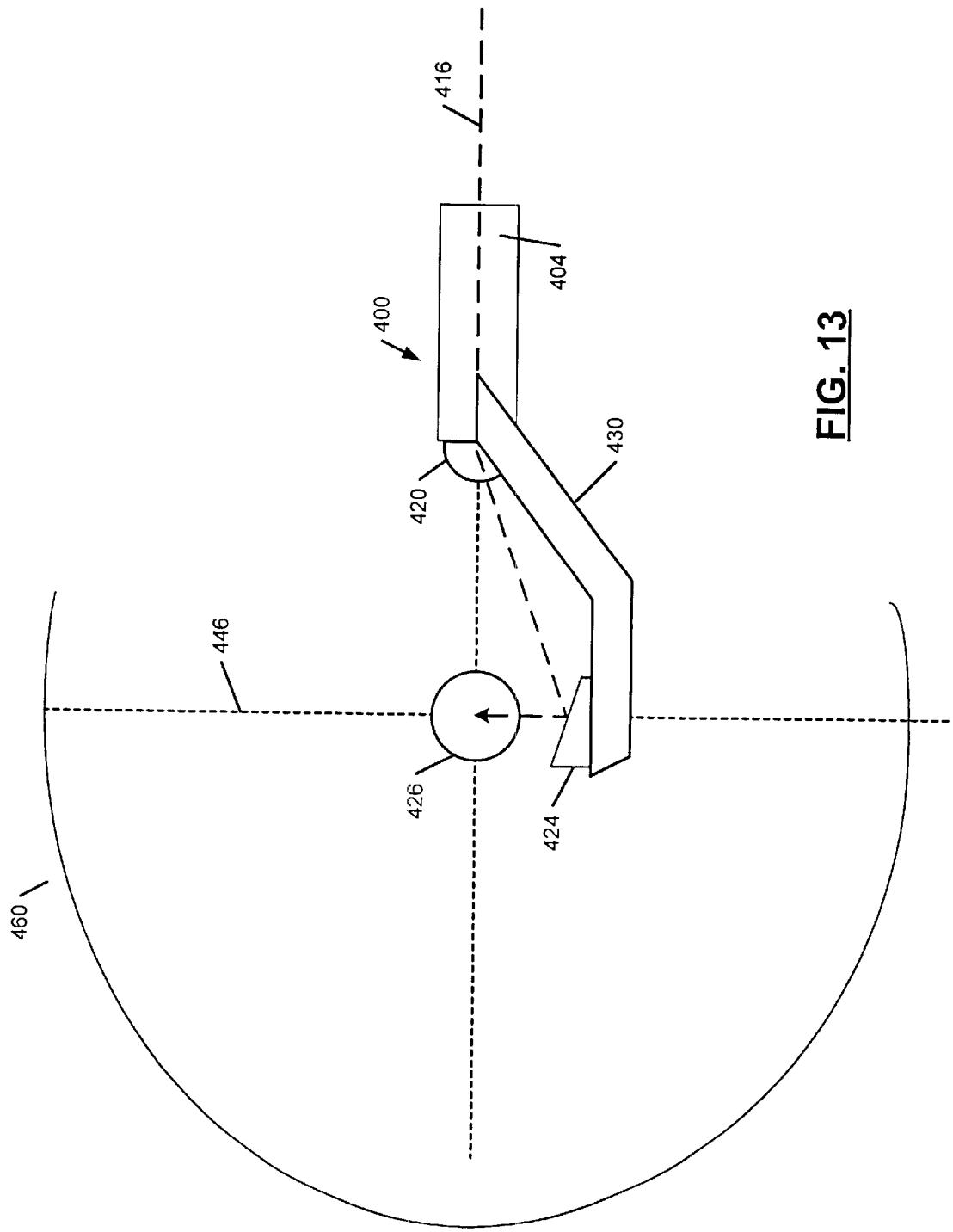
FIG. 13 is a plan view of the mirror arm of FIG. 10 used with a single ellipsoid mirror.
Figure 14:
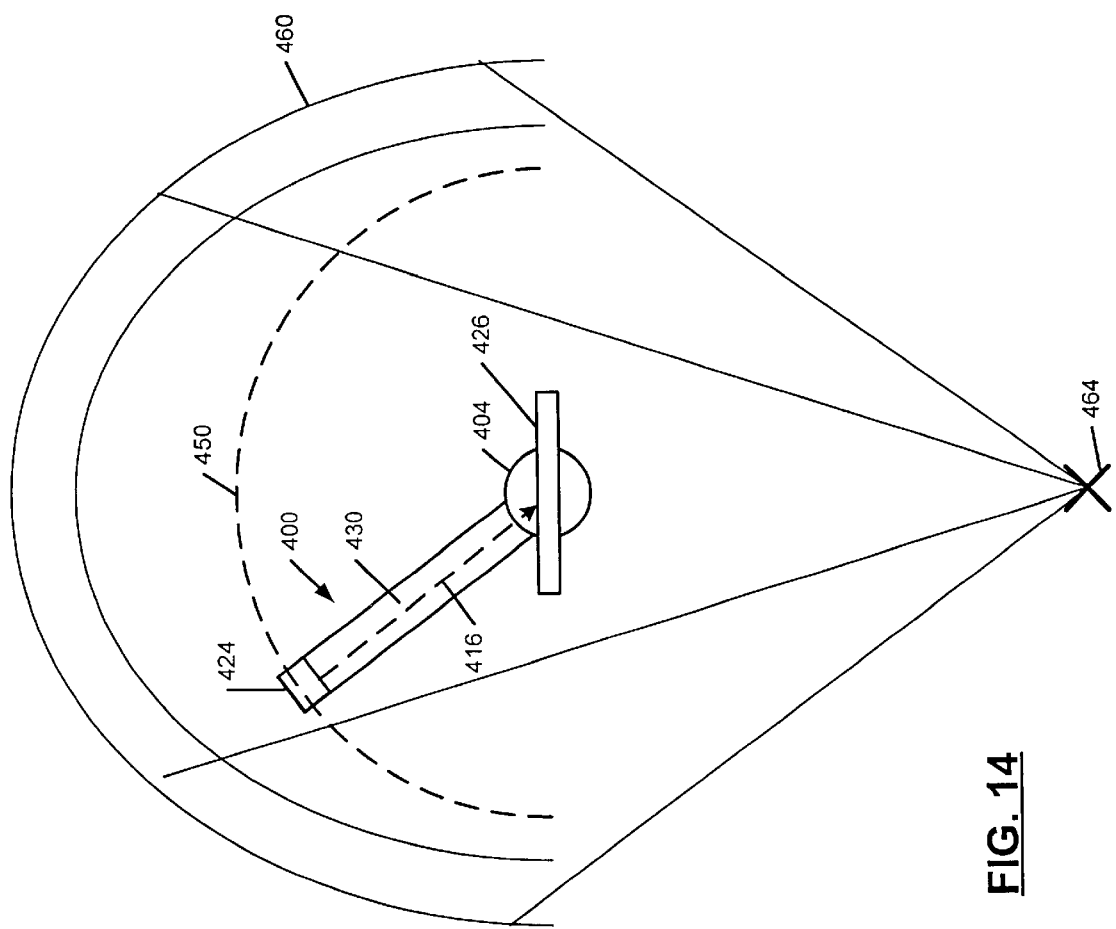
FIG. 14 is a side view of the mirror arm and the single ellipsoid mirror of FIG. 13.

Referring now to FIGS. 13 and 14, the mirror arm 400 of FIG. 10 is rotatably mounted and extends inside or below a single ellipsoid mirror 460 having a focus 464. As can be appreciated, the single ellipsoid mirror 460 reduces the complexity of the reflectometer by eliminating the need for multiple imaging arrays and their associated electronics. While the mirror 460 misses many of the outgoing rays, reflection at those angles can be determined by reciprocity as discussed below.

Referring now to FIG. 15A, an incident beam of light 470 travels in incidence plane 474 onto an anisotropic sample 426. The anisotropic sample 426 (having an orientation indicated by lines 478) reflects a reflected beam of light 482 at a first angle 488 in reflectance plane 490. If an obstruction 492 is located in the reflected plane 490, reflectance properties of the sample cannot be measured for the first angle unless another technique is employed.

Referring now to FIG. 15B, the reciprocity principle states that the anisotropic sample 426 will have the same reflectance characteristics when the source and the detector locations are interchanged. In other words, an incident beam of light 500 replaces the reflected beam of light 482 in FIG. 15A. A reflected beam of light 502 replaces the incident beam of light 470 in FIG. 15A. This particular configuration can not be realized because the mirror arm only allows the beam to be incident in plane 474. However, as discussed below an equivalent configuration can be realized simply by turning the sample.

Referring now to FIG. 15C, the reciprocity principle can be employed in a modified fashion. The anisotropic material 426 is rotated such that the incident beam 510 forms the same angle with the sample 426. The reflected beam 512 is measured at an angle equal to the first angle 488 (identified at 514 in FIG. 15C) on an opposite side of the incidence plane. Thus, the configuration in 15C permits successful measurement of the reflectance value that could not be measured in 15A due to obstruction.

Figure 17:
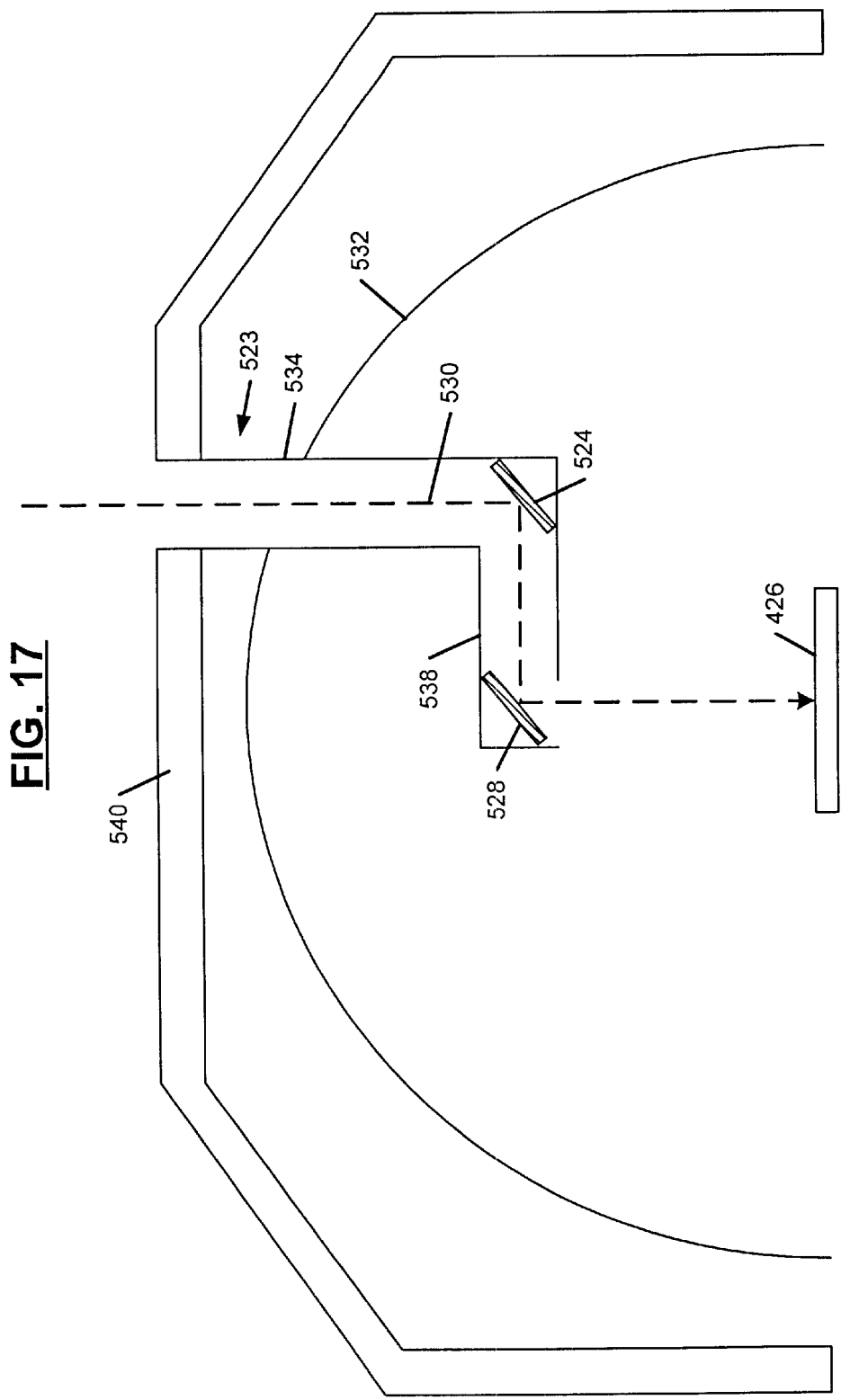
FIG. 17 illustrates a side view of the ellipsoid mirror with the offset slot of FIG. 16.

Referring now to FIGS. 16 and 17, an offset slot 520 is a shown in an elliptical mirror 522. An offset slot mirror arm 523 includes a first mirror 524 and a second mirror 528. The first and second mirrors 524 and 528 redirect an incident beam of light 530 through an elliptical reflector assembly onto the sample 426. The first and second mirrors 524 and 528 are attached to and supported by tubes 534 and 538. The tubes 534 and 538 are attached to an arm 540 that is positioned using stepper motors and encoders in a manner similar to the arms 130 and 132. By the method described above, reciprocity can be used to fill in reflectance values at the outgoing angles obscured by the offset slot 520 and arm 523.

Using conventional measurement methods and apparatus, a complete characterization of the BRDF for a test material requires over 65 million separate measurements when using a two degree increment for the source and the detector. If each individual measurement could be accomplished by the conventional devices in one second, the complete measurement of the BRDF function would take over 2 years. By contrast, the imaging reflectometer according to the present invention can accomplish the task in 8 hours or less assuming a five second measurement at each combination of source incident angle and sample azimuth. Isotropic materials can be fully characterized in under four minutes since the BRDF function is independent of sample azimuth.

For anistropic test materials, the present invention generates the complete hemispherical image signal that is the angular image for a given incident angle and a given azimuth angle. In other words, for the given incident angle and the given azimuth angle, the present invention records all of the variables associated with the reflected light at the same time. As a result, the BRDF measurements can be completed more quickly. For isotropic materials, the BRDF is independent of the azimuth angle. Therefore, only the incident angle is varied when measuring the BRDF.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, specifications and following claims.

What is claimed is:

1. A reflectometer for characterizing reflectance properties of a test material, comprising:

a radiation subsystem that generates and directs radiation onto a test material at a plurality of incident angles;

an elliptical reflector assembly having a first reflector with a first and second foci;

a holder that positions said test material at said first focus of said first reflector; and a first lens that is located within a first focal length of said second focus of said first reflector and that receives a first angular image that is reflected by said first reflector.

2. The reflectometer of claim 1 wherein said elliptical reflector assembly further includes a second reflector having a third and fourth foci, and wherein said holder positions said test material at said third focus.

3. The reflectometer of claim 2 further comprising:

a second lens that is located within a second focal length of said fourth focus of said second reflector and that receives a second angular image that is reflected by said second reflector.

4. The reflectometer of claim 1 wherein said holder is rotatable relative to said radiation subsystem.

5. The reflectometer of claim 3 wherein said first and third foci are approximately co-located on said test material.

6. The reflectometer of claim 3 wherein said radiation subsystem further comprises:

a housing that is moveable relative to said elliptical reflector assembly to alter said incident angle; and a focusing mirror that is connected to said housing.

7. The reflectometer of claim 6 wherein said radiation subsystem further comprises:

a slit that controls a shape of said radiation that illuminates said test material and that is moveable relative to said housing to keep said shape relatively constant as said housing moves.

8. The reflectometer of claim 7 further comprising:

a cam connected to said elliptical reflector assembly; and an arm that is biased by said cam to move said slit.

9. The reflectometer of claim 1 further comprising:
a shutter that blocks said radiation when in a closed position and that passes said radiation when said shutter is in an open position.

10. The reflectometer of claim 6 further comprising:
a first stepper motor that adjusts an angular position of said housing relative to said elliptical reflector assembly to adjust an incident angle of said radiation on said test material.

11. The reflectometer of claim 10 further comprising:
a first position encoder for generating a position signal that is related to the angular position of said housing.

12. The reflectometer of claim 1 wherein said elliptical reflector assembly includes a slot through which said radiation passes.

13. The reflectometer of claim 11 further comprising:
a second stepper motor that adjusts an angular position of said holder.

14. The reflectometer of claim 13 further comprising:
a second position encoder for generating a position signal related to said angular position of said holder.

15. The reflectometer of claim 14 further comprising:
a computer that is connected to said first and second stepper motors and said first and second position encoders;
a first imaging assembly that receives said first angular image and generates a first angular image signal;
a second imaging assembly that receives said second angular image and generates a second angular image signal,
wherein said computer generates a first difference signal by subtracting an ambient first image signal from said first image signal and a second difference signal by subtracting an ambient second image signal from said second image signal.

16. The reflectometer of claim 15 wherein said computer generates a calibrated first product signal by multiplying said first difference signal by a first set of calibration factors and generates a calibrated second product signal by multiplying said second difference signal by a second set of calibration factors.

17. The reflectometer of claim 16 wherein said computer combines said calibrated first difference signal with said calibrated second difference signal to create a hemispherical angular image signal.

18. A method for characterizing reflectance properties of a test material, comprising the steps of:
generating and directing a radiation beam onto said test material at an incident angle;
reflecting radiation that is reflected by said test material using a first reflector with first and second foci;
positioning said test material at said first focus of said first reflector; and
receiving a first angular image that is reflected by said first reflector using a first lens.

19. The method of claim 18 further comprising the steps of:
reflecting radiation that is reflected by said test material using a second reflector with third and fourth foci;
positioning said test material at said third focus of said second reflector; and
receiving a second angular image that is reflected by said second reflector using a second lens.

20. The method of claim 19 further comprising the steps of:
incrementally changing said incident angle; and
adjusting said beam of radiation to keep a shape of said radiation on said test material relatively constant as said incident angle is changed.

21. The method of claim 20 further comprising the steps of:
incrementally rotating said test material.

22. The method of claim 21 further comprising the steps of:
generating a first image signal from said first angular image;
generating a second image signal from said second angular image;
generating a first difference signal by subtracting an ambient first image signal from said first image signal; and
generating a second difference signal by subtracting an ambient second image signal from said second image signal.

23. The method of claim 22 further comprising the steps of:
generating a calibrated first product signal by multiplying said first difference signal by a first set of calibration factors; and
generating a calibrated second product signal by multiplying said second difference signal by a second set of calibration factors.

24. The method of claim 23 further comprising the steps of:
combining said calibrated first difference signal with said calibrated second difference signal to create a hemispherical image signal.

* * * * *